(12) United States Patent
Korporaal (10) Patent No.: US 9,050,055 B2
(45) Date of Patent: Jun. 9, 2015

(54) DETERMINING A PATIENT-SPECIFIC CONTRAST MEDIUM IMPULSE RESPONSE FUNCTION

(71) Applicant: SIEMENS AKTIENGESELLSCHAFT, Munich (DE)

(72) Inventor: Johannes Georg Korporaal, Forchheim (DE)

(73) Assignee: Siemens Aktiengsellschaft, Munich (DE)

( * ) Notice: Subject to any disclaimer, the term of this patent is extended or adjusted under 35 U.S.C. 154(b) by 115 days.

(21) Appl. No.: 13/875,378

(22) Filed: May 2, 2013

(65) Prior Publication Data

US 2013/0324845 A1 Dec. 5, 2013

(30) Foreign Application Priority Data

Jun. 4, 2012 (DE) .......................... 10 2012 209 410

(51) Int. Cl.
*A61B 6/03* (2006.01)
*A61B 6/00* (2006.01)
(Continued)

(52) U.S. Cl.
CPC ................ *A61B 6/481* (2013.01); *A61B 6/486* (2013.01); *A61B 6/507* (2013.01); *G06F 19/34* (2013.01); *A61B 6/488* (2013.01); *A61B 6/032* (2013.01); *A61B 6/037* (2013.01)

(58) Field of Classification Search
CPC ........ A61B 6/481; A61B 6/488; A61B 6/486; A61B 6/032; G06F 19/34
See application file for complete search history.

(56) References Cited

U.S. PATENT DOCUMENTS 5,687,208 A * 11/1997 Bae et al. ........................ 378/8

7,974,682 B2 * 7/2011 Gonzalez Molezzi et al. ............................. 600/432
(Continued)

FOREIGN PATENT DOCUMENTS

CN  101084036 A  12/2007
CN  101277648 A  10/2008
(Continued)

OTHER PUBLICATIONS

Fleischmann, Dominik et.al., "Mathematical Analysis of Arterial Enhancement and Optimization of Bolus Geometry for CT Angiography Using the Discrete Fourier Transform"; in: Journal of Computer Assisted Tomography, Lippincott Williams & Wilkins; 1999, vol. 23, No. 3, pp. 474-484.
(Continued)

*Primary Examiner* — Long V Le
*Assistant Examiner* — Angela M Hoffa
(74) *Attorney, Agent, or Firm* — Harness, Dickey & Pierce, P.L.C.

(57) ABSTRACT

A method for determining a patient-specific contrast medium impulse response function includes providing patient-specific test bolus contrast medium behavior data and a number of basic impulse response functions on the basis of a defined test bolus input function. Simulated test bolus contrast medium behavior functions are generated by combining the basic impulse response functions with the test bolus input function. The simulated functions and the patient-specific data are fitted to one another by varying a number of fitting parameters to obtain optimum fitting parameter values, and the patient-specific contrast medium impulse response function is then created based on the basic impulse response functions and the optimum fitting parameter values. A method for predicting a likely contrast medium behavior and a method for controlling a medical imaging system are also described. Additionally a corresponding apparatus, a control device and an imaging system having such a control device are also described.

20 Claims, 5 Drawing Sheets

(51) Int. Cl.
*A61M 5/00* (2006.01)
*G06F 19/00* (2011.01)

(56) References Cited

U.S. PATENT DOCUMENTS

| | | | | |
|---|---|---|---|---|
| 8,208,699 | B2* | 6/2012 | Hay et al. | 382/128 |
| 8,295,914 | B2* | 10/2012 | Kalafut et al. | 600/431 |
| 8,755,865 | B2* | 6/2014 | Gonzalez Molezzi et al. | 600/431 |
| 2002/0111550 | A1* | 8/2002 | Schwamm et al. | 600/419 |
| 2007/0066892 | A1 | 3/2007 | Haras | |
| 2007/0255135 | A1* | 11/2007 | Kalafut et al. | 600/431 |
| 2008/0097197 | A1* | 4/2008 | Kalafut et al. | 600/431 |
| 2008/0253634 | A1 | 10/2008 | Hay et al. | |
| 2009/0124898 | A1* | 5/2009 | Stodilka et al. | 600/431 |
| 2010/0030073 | A1 | 2/2010 | Kalafut | |
| 2010/0286504 | A1 | 11/2010 | Mistretta et al. | |
| 2011/0130668 | A1 | 6/2011 | Ohyu et al. | |
| 2012/0095328 | A1* | 4/2012 | Lee et al. | 600/420 |
| 2012/0141005 | A1* | 6/2012 | Djeridane et al. | 382/131 |
| 2014/0206991 | A1* | 7/2014 | Korporaal | 600/431 |

FOREIGN PATENT DOCUMENTS

| | | |
|---|---|---|
| CN | 101573629 A | 11/2009 |
| WO | WO 2011163578 A2 | 12/2011 |

OTHER PUBLICATIONS

Mahnken Andreas H., "Quantitative prediction of contrast enhancement from test bolus data in cardiac MSCT", in: Eur. Radiol. 2007, 17, pp. 1310-1319.

Kim S. M. et al., "Interindividual variablility of arterial impulse response to intravenous injection of nonionic contrast agent (Iohexol) in DCE-CT study", in: Medical Physics 2009, 36(10), pp. 4791-4802.

Lee Joseph K.T. et al.: "Computed Body Tomography with MRI Correlation", 3rd ed. Philadelphia Lippincott-Raven, 1998, pp. 1-2.

Galanski M. et al.: "Renal Arterial Stenoses: Spiral CT Angiography", Radiology 1993, vol. 189, No. 1, pp. 185-192, Bibliographic Links.

Bae K.T. et al: "Aortic and Hepatic Contrast Medium Enhancement at CT, Part I. Prediction with a Computer Model", Radiology 1998, vol. 207, pp. 647-655.

Bae K.T. et al.: "Aortic and Hepatic Contrast Medium Enhancement at CT, Part II. Effect of Reduced Cardiac Output in a Porcine Model", Radiology 1998; vol. 207, pp. 657-662.

Blomley M.J.K. et al.: "Bolus dynamics: theoretical and experimental aspects", British Journal of Radiology, 1997, vol. 70, pp. 351-359.

Sheiman R.G. et al.: "Comparison of Tailored and Empiric Scan Delays for CT Angiography of the Abdomen", AJR Sep. 1996, vol. 167, pp. 725-729.

Claves J.L. et al.: "Evaluation of Contrast Densities in the Diagnosis of Carotid Stenosis by CT Angiography", AJR: 169, Aug. 1997, pp. 569-573.

Rubin G.D. et al.: "Measurement of the Aorta and Its Branches with Helical CT", Radiology 1998, vol. 206, pp. 823-829.

Heiken J.P. et al.: "Dynamic Incremental CT: Effect of Volume and Concentration of Contrast Material and Patient Weight on Hepatic Enhancement", Radiology 1995, vol. 195, pp. 353-357.

Claussen C.D. et al.: "Bolus Geometry and Dynamics after Intravenous Contrast Medium Injection", Radiology 1984, vol. 153, pp. 365-368.

Rubin G.D. et al.: "Three-dimensional Spiral CT Angiography of the Abdomen: Initial Clinical Experience", Radiology 1993, vol. 186: pp. 147-152.

Blomley M.J.K. et al: "Contrast Bolus Dynamic Computed Tomography for the Measurement of Solid Organ Perfusion", Invest. Radiol. 1993; vol. 28 (suppl. 5), pp. 72-78.

Bracewell R.N.: "The Fourier transform and its applications, Chapter 6: The basic theorems", 2nd et. New York: McGraw-Hill, 1986: pp. 98-121.

Bae Kyongtae T. et al.: "Aortic and Hepatic Peak Enhancement at CT: Effect of Contrast Medium Injection Rate—Pharmacokinetic Analysis and Experimental Porcine Model", Radiology 1998, vol. 206, pp. 455-464.

Hoe, Lieven van et al.: "Determination of Scan Delay Time in Spiral CT-Angiography: Utility of a Test Bolus Injection", Journal of Computer Assisted Tomography, 19(2), Mar./Apr. 1995 pp. 216-220.

Zierler K.L. et al: "Theoretical Basis of Indicator-Dilution Methods for Measuring Flow and Volume", Circulation Research, 1962, vol. 10, pp. 393-407.

Thomsons H.K. et al.: "Indicator Transit Time considered as a gamma variate", Circulation Research, 1964, vol. 14, pp. 502-515.

Knopp T.J. et al.: "Transcoronary Intravascular Transport Functions Obtained via a Stable Deconvolution Technique", Annals of Biomedical Engineering, 1976, vol. 4, pp. 44-59.

Dawson P. et al.: "Contrast Agent Pharmacokinetics revisited: I. Reformulation", Acad. Radiol. 1996, vol. 3, pp. S261-S263.

Krause Werner: "Application of Pharmacokinetics to Computed Tomography, Injection Rates and Schemes: Mono-, Bi-, or Multiphasic?", Invest. Radiol. 1996; vol. 31, pp. 91-100.

Kalafut John F.: "A New Pradigm for the Personalized Delivery of Iodinated Contrast Material at Cardiothoracic Computed Tomography Angiography", University of Pittsburgh 2010, Swanson School of Engineering, Kapitel 4, p. 51.

Ganong W.F., Circulation, Review of medical physiology, 16th ed. Norwalk, Appleton & Lange, 1991, pp. 496-583.

Schnyder P. et al.: "Injection Techniques", Spiral CT of the Chest, M. Remy-Jardin an J. Remy, Springer-Verlag Berlin Heidelberg New York, Medical Radiology, Handbuch der medizinischen Radiologie, ISBN 3-540-59185-0, 1996, pp. 57-75.

Rubin G.D. et al.: "Three-dimensional spiral comuted tomographic angiography: An alternative imaging modality for the abdominal aorta and its branches", Journal of Cascular Surgery, 1993, vol. 16, pp. 656-666.

German Office Action for DE 10 2012 209 410.5 dated Feb. 8, 2013.

* cited by examiner

DETERMINING A PATIENT-SPECIFIC CONTRAST MEDIUM IMPULSE RESPONSE FUNCTION

PRIORITY STATEMENT

The present application hereby claims priority under 35U.S.C. §119 to German patent application number DE 102012209410.5 filed Jun. 4, 2012, the entire contents of which are hereby incorporated herein by reference.

FIELD

At least one embodiment of the invention generally relates to a method and/or an apparatus for determining a patient-specific contrast medium impulse response function. At least one embodiment of the invention also generally relates to a method for predicting a likely contrast medium behavior and/or to a method for controlling a medical imaging system using said likely contrast medium behavior. At least one embodiment of the invention lastly generally relates to a control device for an imaging system, the device having an apparatus for determining a patient-specific contrast medium impulse response function, and/or to an imaging system for producing image data sets of the interior of an examination object using a control device of this kind.

BACKGROUND

Imaging systems which produce images of the interior of an examination object are nowadays a standard feature of modern medicine. Ultrasound systems, magnetic resonance systems, X-ray equipment or X-ray based computed tomography (CT) systems are typically used for this purpose. To facilitate identification of particular structures inside an examination object, contrast media are commonly used and image data of the region of interest (ROI) is produced at one or more points in time as the contrast medium spreads through the examination object. The contrast medium, which spreads, accumulates and dissipates again in a particular manner in or on the particular structures, makes these structures better distinguishable in the images and shows up pathologies or dysfunctions. In addition, particular organs such as blood vessels, for example, or other objects can be more easily segmented in the image data.

For many areas or rather evaluations, precise determination or even control of the accumulation state (often also termed "enhancement") of the contrast medium in a particular object or organ is advantageous or even necessary. This applies particularly to CT angiography, for example, in which the enhancement in the vessels must be defined as accurately as possible. That is to say, on the one hand a certain minimum enhancement shall be achieved so that segmentation of the vessels in the image data can be optimally performed for subsequent evaluation. On the other hand, the enhancement must not be excessively high, in order to ensure that e.g. calcium deposits are not obscured. Also, acquisition of the image data (the CT scan) must be started at the correct point in time so that the tissue is scanned where possible at the time of maximum accumulation/enhancement. In order to achieve this, a reliable prediction of the contrast medium behavior for each individual patient is desirable.

In order to be able to predict the enhancement at a particular point in time as accurately as possible, a so-called test bolus is often injected. The patient or test subject is first given a small amount of contrast medium and then the enhancement in a particular slice, preferably in the region of interest or at least close to this region, is evaluated. In the case of CT scans, only a slice approximately 10 mm thick, generally orthogonal to the body axis, is measured, usually with a low X-ray dose. For CT angiographies this measurement usually takes place such that the enhancement is observed in a transverse section through the aorta at the heart. If other organs are to be examined, the measurement is accordingly carried out preferably in a slice in the vicinity of the respective organ, e.g. a transverse scan in the aorta near the liver in the case of a liver examination. The relevant aorta transverse section is then used as the ROI for the evaluation and the accumulation of the contrast medium as a function of time is observed using the image data in this region. It is then attempted to distill a patient-specific contrast medium impulse response function (usually also termed "patient function") from the thus determined patient-specific test bolus contrast medium behavior data. Using this patient function, the contrast medium behavior for a further contrast medium injection can then be predicted or, conversely, if a particular contrast medium behavior is desired, the injection protocol required for that purpose can be determined. Injection protocol is to be understood as meaning control rules as to how much contrast medium is to be administered at which point in time. The function which describes this contrast medium injection as a function of time is also generally termed "input function".

If, for example, the blood circulation system is considered as a linear time-invariant system, a contrast medium behavior can be described mathematically as a convolution of the input function with the patient function. In order to determine the patient function from the test bolus contrast medium behavior data for a known test bolus input function, a deconvolution in the spectral domain can be carried out, for example, after Fourier transformation of the injection protocol and test bolus contrast medium behavior data. However, this assumes that the test bolus contrast medium behavior data is measured over a sufficiently long period of time and with high temporal resolution so that, for example, the recirculation of the contrast medium is also included in this data. If the temporal resolution is too low or the test bolus contrast medium behavior data is not completely measured for a sufficiently long time, it is very difficult to generate a reliable patient function.

SUMMARY

At least one embodiment of the present invention is directed to creating a simpler method and/or a corresponding apparatus with which a patient-specific contrast medium impulse response function can be reliably determined even with incomplete test bolus contrast medium behavior data.

To determine a patient-specific contrast medium impulse response function, the method according to at least one embodiment of the invention comprises the following steps:

On the one hand, patient-specific test bolus contrast medium behavior data is provided on the basis of a defined test bolus input function. This can be done, for example, by accessing patient-specific test bolus contrast medium behavior data previously stored in a memory. This patient-specific test bolus contrast medium behavior data, i.e. the contrast medium behavior in the patient under examination, needs to be, in at least one embodiment, measured with the test bolus having been administered in a known, precisely defined manner. That is to say, the input function of the test bolus must also be available for the method according to at least one embodiment of the invention, e.g. stored with the patient-specific test bolus contrast medium behavior data.

On the other hand, a number of, i.e. one or more, basic impulse response functions must be provided. These can be stored, for example, in a memory, in particular a database, which can then be accessed in the method. For creating the basic impulse response functions there are various possibilities which will be explained in greater detail below.

A number of, i.e. one or more, simulated test bolus contrast medium behavior functions are then generated by combining the basic impulse response functions with the test bolus input function. This may be done, for example, by convolving the relevant basic impulse response function with the test bolus input function.

These simulated test bolus contrast medium behavior functions and the patient-specific test bolus contrast medium behavior data are then fitted to one another, for which purpose a number of fitting parameters are varied to obtain optimum fitting parameter values. The simulated test bolus contrast medium behavior function is usually fitted to the test bolus contrast medium behavior data here. In principle, however, the inverse variant or a combination of both procedures would also be possible. The preferred fitting parameters will also be explained in greater detail below.

Finally the patient-specific contrast medium impulse response function is generated on the basis of the basic impulse response functions used and the optimum fitting parameter values.

An apparatus according to at least one embodiment of the invention, for automatically determining a patient-specific contrast medium impulse response function, comprises at least the following components:

An input interface for importing patient-specific test bolus contrast medium behavior data, based on a defined test bolus input function. This can be an interface to a memory in which the relevant data is stored, but also an interface to a processor unit in which the measurement data from a test bolus scan is currently being evaluated and from which the data can be transferred directly.

An input interface for importing a number of basic impulse response functions. This can again be an interface to a memory. In principle, the input interface for importing the test bolus contrast medium behavior data and the input interface for importing the basic impulse response functions can also be implemented as a common interface.

A simulation unit for generating a number of simulated test bolus contrast medium behavior functions by combining the basic impulse response functions with the test bolus input function.

A fitting unit for fitting the simulated test bolus contrast medium behavior function and the patient-specific test bolus contrast medium behavior data by varying a number of fitting parameters to obtain optimum fitting parameter values.

An impulse response function calculation unit for generating the patient-specific contrast medium impulse response function on the basis of the basic impulse response function and the optimum fitting parameter values.

A control device for an imaging system of at least one embodiment of the invention, comprises an interface for acquiring or outputting a contrast medium injection start time, an apparatus for determining a patient-specific contrast medium impulse response function (CIR), and a reference time determination device for determining a reference time for the imaging system based on the contrast medium injection start time and the patient-specific contrast medium impulse response function (CIR).

An imaging system of at least one embodiment of the invention, for producing image data sets of the interior of an examination object, comprises the control device.

A computer program product of at least one embodiment of the invention, can be loaded directly into a memory of a control device of an imaging system, and comprises program code segments for carrying out all the steps of an embodiment of the method when the program product is run on the control device.

BRIEF DESCRIPTION OF THE DRAWINGS

The invention will now be explained in greater detail with reference to exemplary embodiments and the accompanying drawings in which.

DETAILED DESCRIPTION OF THE EXAMPLE EMBODIMENTS

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

To determine a patient-specific contrast medium impulse response function, the method according to at least one embodiment of the invention comprises the following steps:

On the one hand, patient-specific test bolus contrast medium behavior data is provided on the basis of a defined test bolus input function. This can be done, for example, by accessing patient-specific test bolus contrast medium behavior data previously stored in a memory. This patient-specific test bolus contrast medium behavior data, i.e. the contrast medium behavior in the patient under examination, needs to be, in at least one embodiment, measured with the test bolus having been administered in a known, precisely defined manner. That is to say, the input function of the test bolus must also be available for the method according to at least one embodiment of the invention, e.g. stored with the patient-specific test bolus contrast medium behavior data.

On the other hand, a number of, i.e. one or more, basic impulse response functions must be provided. These can be stored, for example, in a memory, in particular a database, which can then be accessed in the method. For creating the basic impulse response functions there are various possibilities which will be explained in greater detail below.

A number of, i.e. one or more, simulated test bolus contrast medium behavior functions are then generated by combining the basic impulse response functions with the test bolus input function. This may be done, for example, by convolving the relevant basic impulse response function with the test bolus input function.

These simulated test bolus contrast medium behavior functions and the patient-specific test bolus contrast medium behavior data are then fitted to one another, for which purpose a number of fitting parameters are varied to obtain optimum fitting parameter values. The simulated test bolus contrast medium behavior function is usually fitted to the test bolus contrast medium behavior data here. In principle, however, the inverse variant or a combination of both procedures would also be possible. The preferred fitting parameters will also be explained in greater detail below.

Finally the patient-specific contrast medium impulse response function is generated on the basis of the basic impulse response functions used and the optimum fitting parameter values.

This method of at least one embodiment therefore no longer requires a mathematical deconvolution and therefore the complete test bolus contrast medium behavior data in maximally high temporal resolution. Instead, a reduced amount of test bolus contrast medium behavior data with relatively large time intervals is also sufficient, and possibly also only in sub-regions, as ultimately the essential point of the method is based on the fitting of one or more simulated test bolus contrast medium behavior functions. With sub-optimum test bolus contrast medium behavior data, the method as a whole is therefore considerably more stable and less delicate than back-calculation via a deconvolution. The inventive method of at least one embodiment for determining a patient-specific contrast medium impulse response function can preferably be carried out fully automatically.

In addition, this method can then be used as part of an inventive method of at least one embodiment for automatically predicting a likely contrast medium behavior. For this purpose, the contrast medium impulse response function determined using this method can be combined, e.g. convolved, with an input function used during the subsequent examination. In this way, in a particular region in which the contrast medium impulse response function has also been determined previously, i.e. from which the test bolus contrast medium behavior data originates, and in the associated organs and objects, the changes in contrast medium accumulation over time can therefore be relatively reliably predicted during the subsequent examination.

Such a method can then in turn be advantageously used in an inventive method, of at least one embodiment, for automatically controlling a medical imaging system, wherein a reference time—e.g. a start time for image acquisition in a particular region—can be determined for the imaging system on the basis of a contrast medium injection start time and the predicted contrast medium behavior. However, determining such a reference time may also be useful for other methods, e.g. for subsequent evaluation of image data sets of contrast medium uptake. Thus in many cases it is essential to know the phase in which particular images were taken, e.g. whether it is a phase in which the contrast medium is spreading or accumulating for the first time in a particular structure, or whether the images were produced in a phase in which the contrast medium is disappearing again from the structure, i.e. is being dissipated.

An apparatus according to at least one embodiment of the invention for automatically determining a patient-specific contrast medium impulse response function comprises at least the following components:

An input interface for importing patient-specific test bolus contrast medium behavior data, based on a defined test bolus input function. This can be an interface to a memory in which the relevant data is stored, but also an interface to a processor unit in which the measurement data from a test bolus scan is currently being evaluated and from which the data can be transferred directly.

An input interface for importing a number of basic impulse response functions. This can again be an interface to a memory. In principle, the input interface for importing the test bolus contrast medium behavior data and the input interface for importing the basic impulse response functions can also be implemented as a common interface.

A simulation unit for generating a number of simulated test bolus contrast medium behavior functions by combining the basic impulse response functions with the test bolus input function.

A fitting unit for fitting the simulated test bolus contrast medium behavior function and the patient-specific test bolus contrast medium behavior data by varying a number of fitting parameters to obtain optimum fitting parameter values.

An impulse response function calculation unit for generating the patient-specific contrast medium impulse response function on the basis of the basic impulse response function and the optimum fitting parameter values.

The patient-specific contrast medium impulse response function can then be fed out via an output interface of the apparatus according to at least one embodiment of the invention to other units, for example, which further process the patient-specific contrast medium impulse response function, in particular perform further calculations or store them.

Such an impulse response function determination apparatus for automatically determining a patient-specific contrast medium impulse response function is implemented with particular preference as part of a control device for an imaging system, i.e. the control device itself comprises said apparatus for automatically determining a patient-specific contrast medium impulse response function. In this case the control device preferably also has an interface for detecting or outputting a contrast medium injection start time and a reference time determination device for determining a reference time for the imaging system based on the contrast medium injection start time and the patient-specific contrast medium impulse response function. The advantage of this is that the control device can directly determine fully automatically the contrast medium impulse response function on the basis of the test bolus contrast medium behavior data and can subsequently be used to control the imaging system accordingly such that, during the actual measurement, image data acquisition can commence at the correct point in time after contrast medium injection and/or the image data can be time-linked with the reference time and stored.

In principle, however, an apparatus according to at least one embodiment of the invention for determining a patient-specific contrast medium impulse response function can also be implemented on other computers which, for example, import the required test bolus contrast medium behavior data and basic impulse response functions from other components and are, for example, connected to the imaging system via a network. This is particularly useful if more compute-intensive tasks are to be transferred out of the control device in order to make the computing capacity of the control device fully available for controlling other measurements.

An inventive imaging system, of at least one embodiment, for producing image data of the interior of an examination object preferably comprises a control device as described above which also has an inventive apparatus, of at least one embodiment, for determining a patient-specific contrast medium impulse response function.

In particular, the simulation unit, the fitting unit and the impulse response function calculation unit of the inventive apparatus of at least one embodiment for determining a patient-specific contrast medium impulse response function can each be implemented as software modules on a suitable computer having appropriate storage capabilities. The input interfaces and the output interface can likewise be realized purely in software, provided it is necessary only to transfer the test bolus contrast medium behavior data and basic impulse response functions from, or output the contrast medium impulse response function to, other additional units or memories implemented on the same computer unit. In principle, however, these interfaces can also be implemented as combined hardware/software interfaces in order to implement an external input and output, e.g. hardware interfaces specifically configured using software components. The advantage of a largely software implementation is that, for example, even imaging system control devices currently in use can be simply upgraded by a software update in order to operate in the inventive manner. In this respect the object is also achieved by a computer program product which can be directly loaded into a memory of a programmable control device, and having program sections for carrying out all the steps of the method according to at least one embodiment of the invention when the program is executed in the control device.

The dependent claims each contain advantageous further developments and embodiments of the invention, wherein the claims of one category can also be further developed according to the dependent claims of another category.

As already explained above, there are various possibilities for creating basic impulse response functions. In a particular example embodiment, at least one basic impulse response function based on empirical data is used. With particular preference, this is a population-averaged contrast medium impulse response function. This empirical data can be obtained beforehand on the basis of a plurality of contrast medium measurements on different patients or test subjects, wherein in each case a normal deconvolution method can be used to determine the individual patient functions which are then averaged to produce the contrast medium impulse response function. This simple variant makes it possible to use a basic impulse response function averaged over any statistical patient group that is, for example, representative of all patients.

In another example embodiment variant, a plurality of patient-type-specific basic impulse response functions are provided. In this context, "patient-type-specific" is to be understood as meaning that the basic impulse response function is in some way associated with a particular patient type or rather characteristics of the patient or test subject. In this case the patient-type-specific basic impulse response function is, for example, an impulse response function based only on empirical data from that group, in that e.g. only the impulse response functions of patients or test subjects from the group in question are averaged. In particular, patient-type-specific basic impulse response functions can be provided for specific patient groups having particular attributes such as sex, weight, height, illness, etc. In a current examination, the respective patient or test subject can then be assigned to a suitable group and the patient-type-specific basic impulse response function matching this group can then be used.

As will be explained further below, it is also possible to use within at least one embodiment of the method different patient-type-specific basic impulse response functions for creating different simulated test bolus contrast medium behavior functions and then fit these different test bolus contrast medium behavior functions to the test bolus contrast medium behavior data. Not only the optimum fitting parameter values can be determined here, but also a particularly suitable simulated test bolus contrast medium behavior function and therefore a particularly suitable basic impulse response function can also be selected, on the basis of which the patient-type-specific contrast medium impulse response function can then be created. In this case it is therefore unnecessary to pre-assign the patient or test subject to a group for which a special patient-type-specific basic impulse response function is available.

Preferably, at least one function section correction function for the basic impulse response function can also additionally be used for fitting. Usually an impulse response function has particular significant sections based on particular mechanisms within the blood circulation system. For example, there is a first major peak, the so-called "FPP transit" (FPP=first pass peak) which shows the first transit of the contrast medium through, for example, the observed artery. This is followed by a more or less pronounced minimum and then a smaller maximum with a slowly decreasing behavior. This region is caused by the recirculation of the contrast medium in the body. Therefore, an FPP transit correction function can preferably be used which primarily affects the first region of the basic impulse response function, and/or a recirculation correction function which mainly affects the region resulting from the recirculation. These function section correction functions can, for example, be added to or subtracted from the basic impulse response function using different weights. In particular, the basic impulse response functions with these function section corrections can be fitted using different weights to the test bolus contrast medium behavior data, which is ultimately tantamount to weighted addition or subtraction of the correction functions to/from the basic impulse response function.

Particular fitting parameters have been found to be particularly important for fitting the test bolus contrast medium behavior function to the test bolus contrast medium behavior data or vice versa.

One of these parameters is a time scaling factor which can be used to vary the width of the simulated test bolus contrast medium behavior function along the time axis. In other words, the time axis of this function is compressed or expanded. Another preferred fitting parameter of the simulated test bolus contrast medium behavior function is an offset time with which the simulated test bolus contrast medium behavior function is shifted relative to the test bolus contrast medium behavior data. A third preferred fitting parameter is an amplitude scaling factor with which the simulated test bolus contrast medium behavior function as a whole is scaled in respect of magnitude. It has been found that these three fitting parameters are essentially sufficient for a good fit, so that fitting is preferably performed using these fitting parameters only. When using a plurality of basic impulse response functions or additional function section correction functions, these three parameters can also be varied separately for each of the basic impulse response functions or function section correction functions, i.e. the parameters can in this respect be regarded as vectors whose elements are in each case the parameters for the individual basic impulse response functions or function section correction functions.

Even if it has been pre-specified that these are fitting parameters of the simulated test bolus contrast medium behavior function, it is also possible—as already explained in the introduction—for these fitting parameters to be applied to the patient-specific test bolus contrast medium behavior data in order to achieve a mutual fit.

In a particular example method of at least one embodiment, optimum fitting parameter values for a basic impulse response function are determined using an iterative method, i.e. a FOR-loop is repeatedly executed, for example, within an algorithm of a fit method in order to achieve an optimum fit. At least the following steps are carried out in an iteration step.

a) The basic impulse response function is scaled using a time scaling factor which is the first fitting parameter value.
b) A current simulated test bolus contrast medium behavior function is then determined for the time-scaled basic impulse response function ("current" in this context means the one applicable in the respective iteration step).
c) The current simulated test bolus contrast medium behavior function and the patient-specific test bolus contrast medium behavior data are then fitted to one another by varying a number of additional fitting parameters, preferably an offset time and/or an amplitude scaling factor.

d) A deviation value (also known as "goodness of fit") of the currently fitted simulated test bolus contrast medium behavior function is then determined from the patient-specific test bolus contrast medium behavior data. This deviation value is determined in respect of a defined deviation criterion using, for example, the sum of the least squares method or a similar deviation criterion for this purpose.

e) The parameter value combination of the fitting parameters of the current fitted simulated test bolus contrast medium behavior function is then stored if the calculated deviation value is better than a deviation value of a previously stored parameter value combination, i.e. a smaller deviation is present, for example. It is clear that in the case of a first transit this parameter value combination should always be stored, as no deviation value is yet available for comparison. It is likewise clear that a pointer to the deviation value (i.e. the value itself or a link thereto) of the currently stored parameter value combination must always also be stored for subsequent comparison with other deviation values. In this way it is always ensured that the parameter value combination that has resulted in the best fit is currently stored.

Within at least one embodiment of this iteration method, the time scaling factor is then varied from one iteration step to the next iteration step and the iteration is finally continued until a termination criterion is reached. The termination criterion can be that a particular number of iteration steps have been executed, e.g. that a particular number of fixed time scaling factors have been pre-tested. However, a termination criterion can also be that the deviation value is less than or equal to a particular limit value.

As a result, a suitable parameter value combination is then available in order to determine the desired patient-specific contrast medium impulse response function from the basic impulse response function used or the basic impulse response functions or rather function section correction functions used, with the aid of the parameter values.

As already mentioned above, it is also possible to test out a plurality of basic impulse response functions. For this purpose, in a preferred further variant of at least one embodiment of the method according to the invention, a basic impulse response function is likewise selected using an iterative method, the following method steps being executed in an iteration step:

First a basic impulse response function is selected from a plurality of basic impulse response functions.

Optimum fitting parameter values are then determined for the selected basic impulse response function. With particular preference this can take place in accordance with the above described iterative method.

For this iterative selection of the basic impulse response function, a new basic impulse response function is selected accordingly from the plurality of basic impulse response functions from one iteration step to the next iteration step and the iteration is continued until a termination criterion is reached. The termination criterion is generally reached when all the basic impulse response functions have been tested. In principle, however, it is also possible here to terminate the process if, for example, a sufficiently good deviation value is achieved. In this method, not only must the best parameter value combination be stored, but a pointer to the respective basic impulse response function must also be stored or overwritten.

In the following example embodiments it will be assumed that the imaging system is a computed tomography system which can be used for CT angiography, for example. However, it is expressly pointed out that embodiments of the invention are not limited to use on computed tomography systems, but can also be used with other medical imaging systems such as magnetic resonance systems or ultrasound systems, for example.

Figure 1:
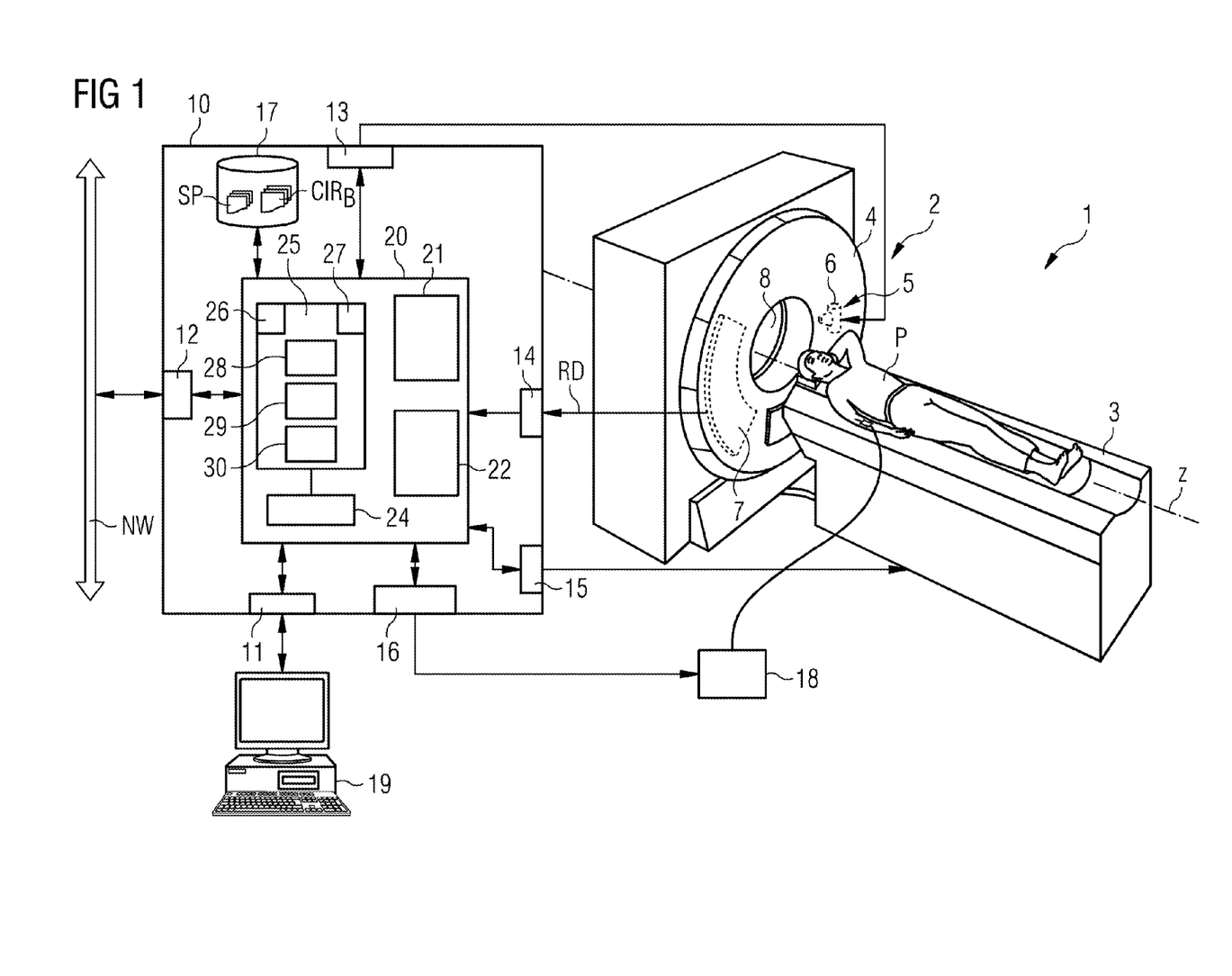
FIG. 1 schematically illustrates an imaging system comprising an embodiment of an inventive apparatus for determining a patient-specific contrast medium impulse response function.

FIG. 1 shows an example of a CT system 1, comprising an apparatus 25 of an embodiment of the invention for determining a patient-specific contrast medium impulse response function. The CT system 1 here has a central control and processing device 10 and a scanner unit 2.

The scanner unit 2 includes a patient table 3 and a gantry housing 4 in which a raw data acquisition device 5 comprising an X-ray source 6 and a detector arrangement 7 disposed opposite one another on a gantry can be rotatably mounted about an examination area 8. An examination object P, here a test person or patient P, on the patient table 3 can be moved into the examination area 8 along a system axis (or more specifically axis of rotation) z.

It is also expressly pointed out that the computed tomography system 1 shown in FIG. 1 is only an example and embodiments of the invention can self-evidently also be used in systems in which the gantry moves along the patient or test person, the latter lying in a fixed position on the table.

Other types of detector can also be used, e.g. detectors extending along the entire circumference and which remain stationary with only the X-ray source 6 rotating. Variants comprising a plurality of X-ray sources or other designs are also possible.

In the example shown, the patient P or test subject is human. However, in principle the method can also be used on animals, i.e. the term test subject or patient is accordingly to be defined in a broad sense.

A contrast medium is administered to the test subject or patient P via an injection needle, wherein the flow rate of the contrast medium as a function of time can be controlled by a contrast medium control unit 18 according to a precisely defined input function which is specified, for example, in an injection protocol.

The gantry with its components is controlled via the central control and processing device 10 which comprises a processor 20 and a plurality of interfaces 11, 12, 13, 14, 15, 16, and a memory 17. Instead of one processor 20, a plurality of interacting processors can of course also be used.

Connected via a first interface 11 is a terminal 19 for operating the computed tomography system 1. Another interface 12 is used to connect to a network NW, e.g. a radiological information system (RIS) network and/or a picture archiving and communication system (PACS) network. Image data and/or raw data can be transmitted over this network NW to mass storage devices, output units, evaluation stations, workstations or the like.

A control interface 13 can be used for transmitting signals via a control line to the gantry and the X-ray source 5 in order to control them appropriately. For the sake of simplicity, a common control interface 13 for all the control tasks relating to the gantry is illustrated schematically only.

In order to produce the respective images in the desired manner, the processor 20 also incorporates a driver 21 realized in software. This driver 21 imports particular scan protocols SP from the memory 17, for example, to control the scanner 2 for a particular measurement. A control and processing unit 10 for a computed tomography system usually has a memory 17 containing a plurality of such scan protocols SP for a wide variety of examination situations, wherein the operator can select and possibly modify a suitable scan protocol SP via the terminal 19. Once scanning has started, the entire computed tomography system 1 operates in accordance with the control parameters in the scan protocol SP selected. However, the operator can monitor and control the entire system at all times via the terminal 19.

The raw data RD, i.e. projection measurement data, is acquired from the detector arrangement 7 via a data line at appropriate times over a raw data acquisition interface 14. The measured raw data RD is transmitted to an image reconstruction unit 22 which creates therefrom the image data sets and writes them, for example, to DICOM files or other image files which are then available for various other functions. These functions include, for example, saving in the internal memory 17 or an external memory via the NW, displaying on the screen of the terminal 19, but also automatic evaluation, e.g. segmentation and/or determination of contrast medium accumulation values in a pre-defined region of interest (ROI). This ROI may have been manually defined, for example, by a user after display on a terminal 19 using a graphical user interface. However, automatic selection of the ROI is also possible.

Via another control interface 15, the table advance can be controlled to match the control of the gantry, X-ray source 6 and detector arrangement 7 in order thus to acquire raw data RD from the desired region of the examination object P, e.g. in the heart region in the case of CT angiography, in a sequential process or in a helical process (spiral CT) depending on the control protocol, for example, and reconstruct the image data therefrom. Both individual slices and volume data can be captured.

Another interface 16 enables the external contrast medium control unit 18 to be controlled in synchronism with the other units of the computed tomography system 1 via the control and processing unit 10. Alternatively, the contrast medium control unit 18 can also be part of the control and processing unit 10.

In the example shown, an impulse response function determination apparatus 25 for automatically determining a patient-specific contrast medium impulse response function is implemented in the processor 20 of the control and processing unit 10. This apparatus has an input interface 26 for importing patient-specific test bolus contrast medium behavior data, and an input interface 27 for importing a number of basic impulse response functions which can be stored, for example, in the memory 17. In addition, the apparatus 25 comprises a simulation unit 28 for generating a number of simulated test bolus contrast medium behavior functions, a fitting unit 29 for fitting the simulated test bolus contrast medium behavior functions and the patient-specific test bolus contrast medium behavior data to one another, and an impulse response function calculation unit 30 for creating the patient-specific contrast medium impulse response function.

Also implemented here in the processor 20 of the control and processing unit 10, likewise in software form, is a reference time determination device 24 for determining a reference time for the imaging system 1 based on a contrast medium injection start time. The precise mode of operation of the apparatus 25 for automatically determining a patient-specific contrast medium impulse response function and of the reference time determination device 24 will be explained in greater detail below with reference to FIGS. 2 to 8.

The image reconstruction unit 22, the apparatus 25 for automatically determining a patient-specific contrast medium impulse response function and the reference time determination device 24 are here realized in software form on the processor 20. In principle, however, all these units can also be implemented as discrete hardware components or on another computer connected to the network NW to which computer the raw data is first transmitted via the network NW. The advantage of transferring all or part of the image processing to an external workstation is that the control device 10 has less workload and is therefore available more quickly for further scans.

It is clear that a CT system 1 used for an embodiment of the invention may also have a large number of other usual components which, however, for reasons of simplicity are not shown in FIG. 1 and do not need to be explained in greater detail, as they will be familiar to the average person skilled in the art.

Figure 2:
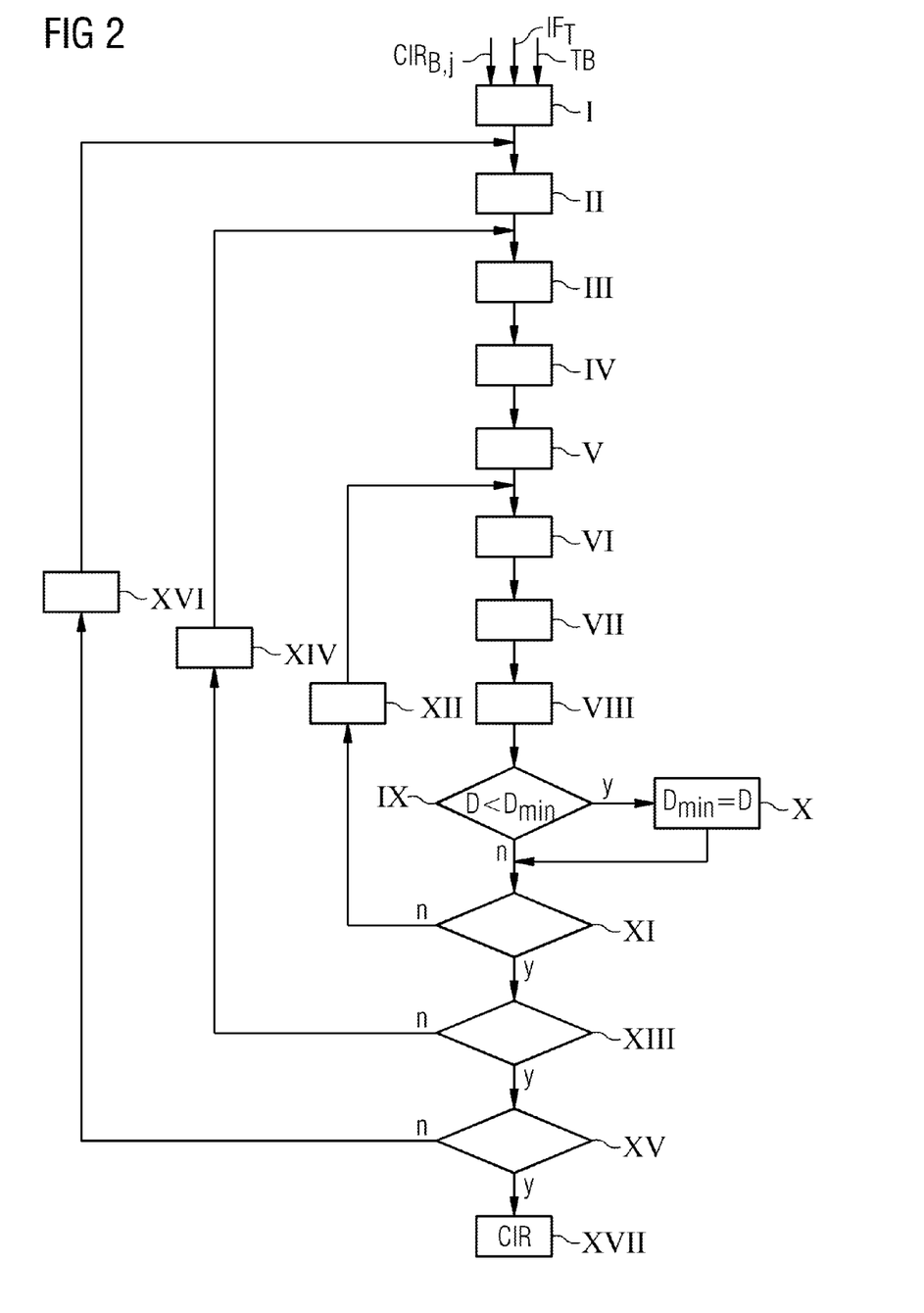
FIG. 2 shows a flow chart of a possible sequence of an embodiment of an inventive method for determining a patient-specific contrast medium impulse response function.

FIG. 2 shows the sequence of an example embodiment of the inventive method for determining a patient-specific contrast medium impulse response function CIR. This is a multi-nested iterative method (having at total of three iteration loops which can be programmed e.g. as FOR-loops), wherein among other things an ideal basic impulse response function CIRB,m is selected from a plurality of possible basic impulse response functions CIRB,m and the optimum fitting parameter values are simultaneously determined therefor in order to then obtain therefrom the patient-specific contrast medium impulse response function CIR.

The method begins in step I with initially the possible basic impulse response functions CIRB,m being loaded and a first basic impulse response function CIRB,1 (with j=1, 2, 3, . . . ) being selected from a number of basic impulse response functions CIRB,j.

Figure 3:
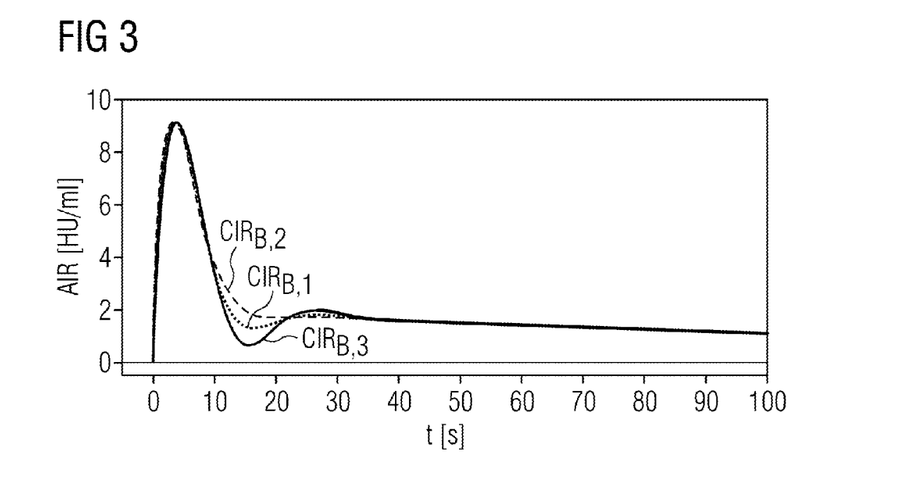
FIG. 3 is a graph showing different possible basic impulse response functions which differ in respect of their recirculation trough.

In the graph in FIG. 3, three different possible basic impulse response functions CIRB,1, CIRB,2, CIRB are plotted. These show the arterial impulse response (AIR) in HU/ml (HU=Hounsfield unit) over time t in s. From a particular starting point in time, here zero, such an impulse response function CIRB,1, CIRB,2, CIRB,3 initially shows a steep rise to a maximum value. The function then falls almost as steeply again. This first peak is also known as the first pass peak (FPP). It arises when the contrast medium passes through the artery for the first time at the observed position, i.e. in the scanned slice. Depending on the patient's circulatory system, this is generally followed by a recirculation "trough" of differing depth in the three functions plotted. This is the point in time at which the contrast medium has largely disappeared again from the observed position. This is followed by a new, considerably smaller maximum with a gradual reduction in the contrast medium concentration over the subsequent time. This is the so-called recirculation, when the contrast medium reaches the observed point in the artery in question for a second time. The FPP, the recirculation trough and the significance of the subsequent recirculation maximum are features that can characterize a particular contrast medium impulse response function.

The basic impulse response functions CIRB,m used here are preferably population-averaged functions which are defined for particular discrete times tCIR of a particular temporal resolution $\Delta$tCIR. This temporal resolution should preferably be higher than that of the test bolus data in order thus to achieve a best possible fit. For example, the temporal resolution of the population-averaged basic impulse response functions could be 0.01 s. The different basic impulse response functions CIRB,1, CIRB,2, CIRB,3, e.g. having the different recirculation troughs, may have been created, for example, on the basis of different population groups, e.g. classified according to sex, body weight and/or height.

In addition, in this step I the patient-specific test bolus contrast medium behavior data TB and an associated test bolus input function IFT are also loaded. The test bolus contrast medium behavior data TB was measured, for example, in a previous test scan at the discrete times tTB by administering a contrast medium to the patient or test subject according to the defined test bolus input function IFT and then acquiring raw data to reconstruct image data of a predefined ROI, in the case of a heart examination, for example, in a slice containing an artery as close as possible to the heart. This test measurement may have been initiated, for example, by way of the driver 21 (see FIG. 1) on the basis of a control protocol SP for a test bolus scan and, by means of the reconstruction device 22, corresponding image data then reconstructed which was then evaluated by a corresponding evaluation unit in order to determine the test bolus contrast medium behavior data TB as a function of time. The test bolus input function IFT is generally a simple rectangular function, so, that from a particular start time, a constant dose of contrast medium is injected up to a predefined end time.

In addition, in the first step I, other values required at a later stage of the method (e.g. variables, limit values, etc.) are initialized.

Figure 4:
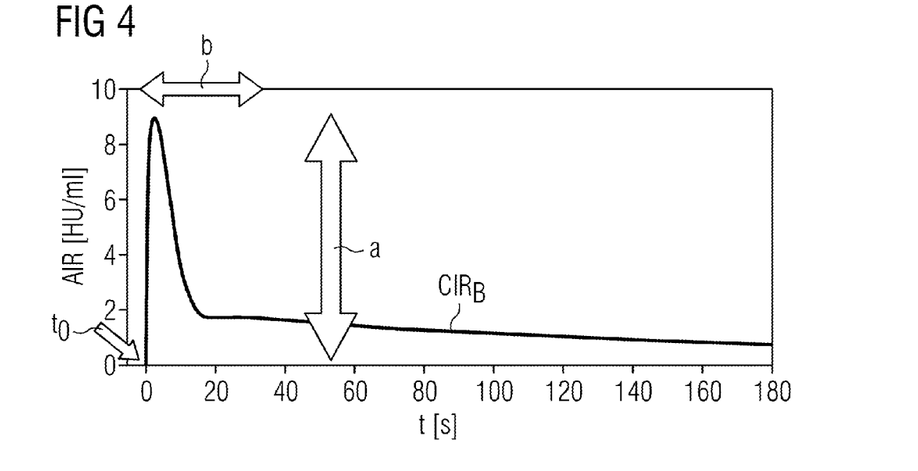
FIG. 4 is a graph showing an example of a basic impulse response function and schematically illustrating possible fitting parameters.

Then, in step II, the first fitting parameter value, namely a time scaling factor b, is first initialized. The reason for this is that the basic impulse response function CIRB,j selected for the iteration of the outer iteration loop is iteratively re-scaled using different time scaling factors around a particular average value in the next middle iteration loop shown in FIG. 2. This time scaling corresponds to compression or elongation of the time axis of the basic impulse response function CIRB, m, as indicated in FIG. 4 by the horizontal double arrow b. FIG. 4 again shows a selected basic impulse response function CIRB in the same manner as the basic impulse response functions CIRB,1, CIRB,2, CIRB,3 in FIG. 3.

In addition to this time scaling factor b, in the further iteration steps in an embodiment of the method according to FIG. 2 an amplitude scaling factor a and an offset time t0 are matched. The offset time t0 relates to a shift in the start time of the basic impulse response function, and the amplitude scaling factor a to a multiplication of the function values by the factor a.

Figure 5:
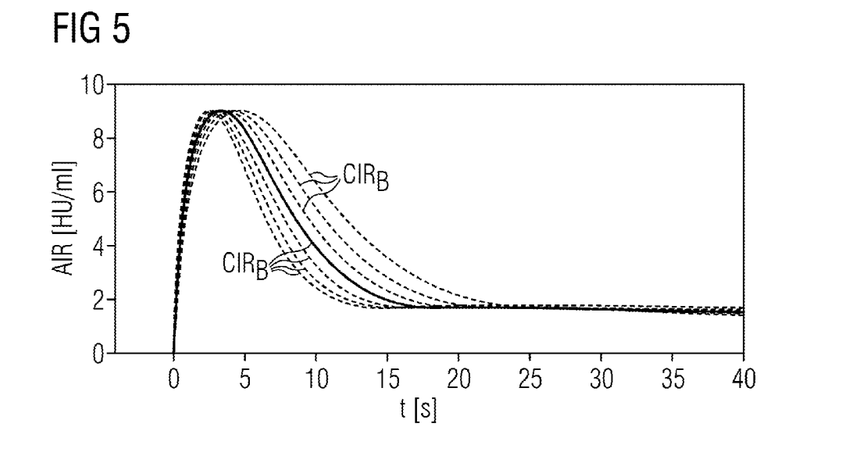
FIG. 5 is a graph showing variants of a basic impulse response function which differ in terms of width, caused by different values of a time scaling factor b.

FIG. 5 plots the effect of compression and elongation of the time axis of the basic impulse response function CIRB by the time scaling factor b, showing the output function (the solid line which corresponds to the function in FIG. 4) and a plurality of variations of this function with different values of b, where b can assume values both greater and less than 1. For the method according to FIG. 2, the start value for the first iteration pass in step II can be set to b=0.5, for example. In each iteration loop, b can be incremented by a value of 0.1 up to e.g. a value of b=2.5. However, other values are also possible.

In step III the selected basic impulse response function CIRB,j(t) is then fitted to the time scaling factor in the time domain by creating a function of the form CIRB,j(b·t).

In step IV a simulated test bolus contrast medium behavior function TFS is then generated by convolving the basic impulse response function CIRB,j(b·t) currently selected in this iteration loop and compressed or elongated using the current time scaling factor b, with the current input function IFT(t):

$$TF_S(t) = IF_T(t) \otimes CIR_{B,j}(b \cdot t) \quad (1)$$

As the basic impulse response function CIRB,j(t) is defined for the discrete points in time tCIR of a particular temporal resolution ΔtCIR, the temporal resolution of the basic impulse response function CIRB,j changes to b·ΔtCIR when it is multiplied by the time scaling factor b. Depending on the type of implementation, it may be necessary to adjust the test bolus input function IFT(t) with which the test bolus contrast medium behavior data TB was produced to this temporal resolution b·ΔtCIR. It may suffice here to determine or define the test bolus input function at the discrete times t=b·tCIR. In this case the simulated test bolus contrast medium behavior function TFS(t) will then have the same temporal resolution b·ΔtCIR as the test bolus input function IFT(t) and the basic impulse response function CIRB,j(b·t).

In step V the maxima of the first peak of the patient-specific test bolus contrast medium behavior data TB and of the simulated test bolus contrast medium behavior function TFS as previously calculated are then overlaid. This can be done by determining the maxima of both the patient-specific measured test bolus contrast medium behavior data TB and the current test bolus contrast medium behavior function TFS and storing the time offset between the two maxima as a peak offset value ΔtP.

In order to achieve the best possible fit of the simulated test bolus contrast medium behavior function TFS to the patient-specific test bolus contrast medium behavior data TB, as part of the simulation method according to FIG. 2 in the inner iteration loop shown there, the simulated test bolus contrast medium behavior function is iteratively shifted around this peak offset value ΔtP in a particular time window using a particular temporal resolution, e.g. 0.5 s. This time window can be, for example, +/−3 s. In other words, as part of the inner iteration loop, the first peak of the test bolus contrast medium behavior function TFS is shifted along within the time window with a defined temporal resolution around the first peak of the patient-specific test bolus contrast medium behavior data TB. For this purpose, in step V a shift value Δtshift is first set which corresponds to the lowest time of the desired time window, e.g. −3 sec.

In step VI the simulated test bolus contrast medium behavior function TFS is then shifted by an offset time t0=ΔtP+Δtshift determined by the peak offset value ΔtP and the time shift value Δtshift and the values of the simulated test bolus contrast medium behavior function TFS(t+t0) are thus determined at the same points in time tTB as the test bolus contrast medium behavior data TB.

In step VII the ideal amplitude scaling factor a is finally determined in order to fit the currently time-shifted and scaled simulated test bolus contrast medium behavior function TFS to the patient-specific test bolus contrast medium behavior data TB. This fit is optimum if the difference between the two, i.e. TB(tTB)−TFS(tTB)·a, is as small as possible. In this optimization problem, the ideal solution for the scaling factor a, in this case a scalar, can be determined using the least squares method (linear least squares), wherein the vector elements of TFS(tTB) and TB(tTB) are in each case the function values at the known points in time tTB:

$$a = (TF_S^T \cdot TF_S)^{-1} \cdot TF_S^T \cdot TB \quad (2)$$

where the superscript "T" stands for a vector transposition.

In step VIII a deviation value D (also known as goodness of fit) is finally determined. This is done here e.g. using a method of least squares deviation of the test bolus data TB from the values of the simulated test bolus contrast medium behavior function TFS at the points in time tTB according to $$D = \sum_{t=t_{TB}} \lfloor (TB(t) - TF_s(t) \cdot a)^2 \rfloor \quad (3)$$

where the values of the test bolus contrast medium behavior function $TF_S(t)$ has been scaled using the amplitude scaling factor a, the current values for b and $t_0$ being implicitly contained in the test bolus contrast medium behavior function $TF_S(t)$.

In step IX it is then checked whether the current deviation value D for the current fit is better than a deviation value Dmin that was stored in a previous pass of the iteration method. It is clear that for a first pass of the iteration loop a comparison value Dmin must be present here which is so large that, in the first pass, the current deviation value is stored in any case for further comparisons. This can be implemented, for example, by initializing the value Dmin to a correspondingly high value in step I above.

If the deviation value D, i.e. the goodness of fit, is better than all the other previous calculations, i.e. the deviation value is less than the previous deviation values (D<Dmin), for example, in step X the current fitting parameter values, namely the current time scaling factor b, the current offset time t0 and the current amplitude scaling factor a, are stored (branch "y"). In addition, a pointer or the like is set to the currently selected basic impulse response function CIRB,j. Finally the current deviation value D is set as the new minimum deviation value Dmin, so that a subsequent comparison with this current deviation value D is made.

Then in step XI it is checked whether all the provided shift values Δtshift have already been run through. If this is not the case (branch "n"), in step XII the time deviation value Δtshift is incremented by a predefined value and the loop is repeated from step VI. Otherwise, this loop is terminated (branch "y") with continuation in step XIII.

If it is established in step IX that the current deviation value D is not less than the previous minimum deviation value Dmin (branch "n"), the loop termination criterion is checked in step XI and if necessary the loop is repeated as from step VI.

In step XIII the termination criterion of the middle loop is checked as to whether all the provided time scaling factors b have been tested. If this is not the case (branch "n"), in step XIV the time scaling factor b is set to the next provided value and the middle loop is repeated as from step III. Otherwise (branch "y") the method proceeds with step XV.

In step XV, a termination criterion for the outer loop is finally checked as to whether all the possible basic impulse response functions CIRB,j have already been tested. If this is not the case (branch "n"), in step XVI the next basic function CIRB,j+1 is selected and the outer loop is repeated as from step II, otherwise (branch "y") in step XVII the desired patient-specific contrast medium impulse response function CIR can finally be created from the selected basic impulse response functions CIRB and the optimum (previously determined in the loops and stored) fitting parameter values t0, b, a in accordance with the following equation $$CIR(t) = a \cdot CIR_B(t_0 + t \cdot b) \qquad (4).$$

Figure 6:
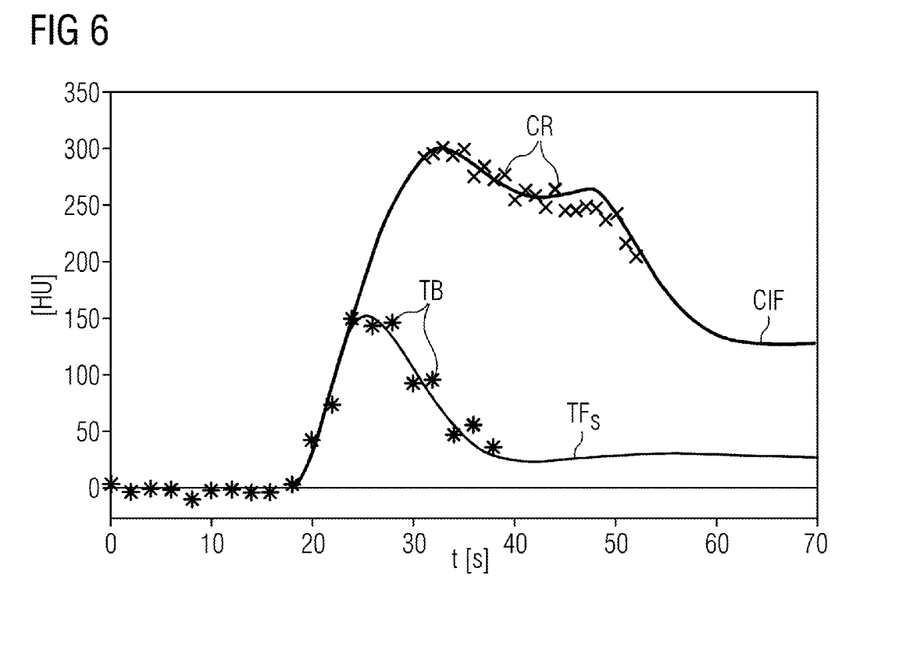
FIG. 6 is a graph showing test bolus contrast medium behavior data and a simulated test bolus contrast medium behavior function fitted thereto, and, based thereon, a predicted contrast medium behavior function in comparison with contrast medium behavior data.

FIG. 6 shows how this calculation method can provide a very good prediction of a likely contrast medium behavior with any input function. The patient-specific test bolus contrast medium behavior data TB of a test bolus measurement is shown here as measuring points in Hounsfield units (HU) over time t in s. To this test bolus contrast medium behavior data TB a test bolus contrast medium behavior function TFS has been fitted as described above.

A patient-specific impulse response function CIR was determined in the manner described above on the basis of this test bolus contrast medium behavior function TFS or rather of the determined fitting parameter values t0, b, a and the basic impulse response function used for this purpose. This contrast medium impulse response function CIR was then convolved in the usual way with the input function IF for the contrast medium examination, wherein a contrast medium behavior prediction in the form of a concentration behavior function CIF is produced which is plotted in FIG. 6 as the upper solid curve. The superposition with the actual concentration behavior data CR measured during the contrast medium examination shows that the prediction agrees very well with the actual contrast medium behavior.

On the basis of the prediction concentration behavior function CIF, any reference time for the imaging system at which the enhancement is maximum at the relevant location for which these functions have been determined can therefore also be determined, for example, by the reference time determination device 24 (see FIG. 1) if the contrast medium input function IF and its injection start time or more specifically contrast medium injection start time are known. Thus, the point in time at which in the case of CT angiography, for example, optimum imaging can take place can be readily determined.

It should be noted at this juncture that the method illustrated in FIG. 2 can also be carried out without using a plurality of different basic impulse response functions. Thus in the simplest case it is sufficient to use a single basic impulse response function, e.g. an averaged curve of the empirical data of a patient group representative of the total population. In this case the outer iteration loop can be omitted. The method involves less computational complexity.

Figure 7:
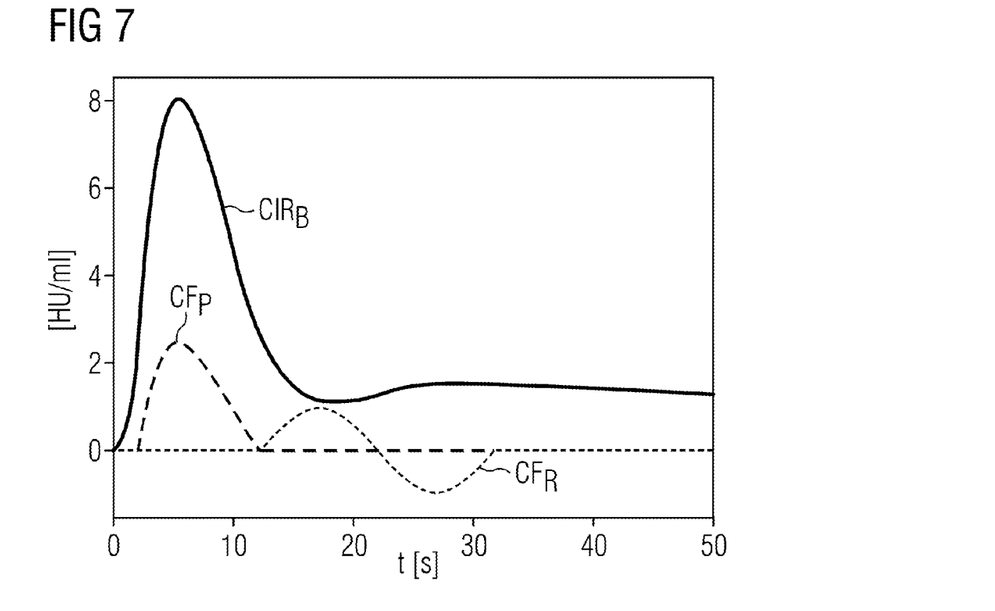
FIG. 7 is a graph showing an example of a basic impulse response function and two function section correction functions.

In order to achieve better matching of the peak shape of the FPP and the recirculation trough, in particular even without using a plurality of basic impulse response functions, function section correction functions can additionally be used, e.g. an FPP transit correction function and a recirculation correction function, which are then fitted using different weights. In other words, variations are then defined on the time sub-domain for a basic impulse response function (or in the case of a particularly exact method also for a plurality of basic impulse response functions selectable as above) in order to correct the FPP and correct the basic impulse response function after or in the recirculation trough. In this connection, FIG. 7 shows a population-averaged basic impulse response function CIRB as well as an FPP transit correction function CFP and a recirculation correction function CFR. The functions CIRB, CFP, CFR here represent the arterial impulse response AIR in HU/ml over time t in s.

The contrast medium impulse response function CIRm is made up of the three functions as follows:

$$CIR_m(t) = CIR_B(t) + CF_P(t) + CF_R(t) \qquad (5)$$

Only the shape of these three curves is critical, but not the initial amplitude, as the amplitude is matched as part of the subsequent fitting method by the amplitude scaling factor a.

The weights of these three functions can be calculated in a step similar to step VII in the method as shown in FIG. 2. In the method according to FIG. 2, the basic impulse response functions CIRB,j(t) and therefore also TFS(t) were only vectors (whose elements were in each case the function values for the discrete times t), as only a population-averaged curve had to be considered as the basic impulse response function for each iteration step.

If a basic impulse response function CIRm(t) is set up as a matrix having three sub-functions, the same fit routine can still be used. For this purpose the contrast medium impulse response function CIRm(t) is defined as follows:

$$CIR_m(b \cdot t) = \begin{pmatrix} CIR_B(b \cdot t_1) & CF_P(b \cdot t_1) & CF_R(b \cdot t_1) \\ CIR_B(b \cdot t_2) & CF_P(b \cdot t_2) & CF_R(b \cdot t_2) \\ \vdots & \vdots & \vdots \\ \vdots & \vdots & \vdots \\ CIR_B(b \cdot t_n) & CF_P(b \cdot t_n) & CF_R(b \cdot t_n) \end{pmatrix} \quad (6)$$

The elements in a column here contain the function values of the corresponding sub-function at the discrete points in time b·t1, b·t2, ..., b·tn. After convolution of the parts with the input function IF (similar to step IV in FIG. 2), this produces for a composite simulated test bolus contrast medium behavior function TFs,m(t):

$$TF_{S,m}(t) = \begin{pmatrix} TF_{S,B}(t_1) & TF_{S,CFP}(t_1) & TF_{S,CFR}(t_1) \\ TF_{S,B}(t_2) & TF_{S,CFP}(t_2) & TF_{S,CFR}(t_2) \\ \vdots & \vdots & \vdots \\ \vdots & \vdots & \vdots \\ TF_{S,B}(t_n) & TF_{S,CFP}(t_n) & TF_{S,CFR}(t_n) \end{pmatrix} \quad (7)$$

In equation (7) TFS,B represents the convolution of the basic impulse response function CIRB with the input function IF, TFS,CPF the convolution of the FPP transit correction function CFP with the input function IF, and TFS,CPR the convolution of the recirculation correction function CFR with the input function IF.

In a step similar to step VII in the method according to FIG. 2, the ideal solution for the scaling factor, in this case a vector, can be determined e.g. in the linear least squares method:

$$\vec{a} = (TF_S^T \cdot TF_S)^{-1} \cdot TF_S^T \cdot TB \quad (8)$$

where the superscript "−1" stands for a matrix inversion and the superscript "T" for a transposed matrix.

All the scaling factors are then obtained as elements into a vector $$\vec{a} = \begin{pmatrix} a_B \\ a_{CFP} \\ a_{CFR} \end{pmatrix} \quad (9)$$

where $a_B$ is the scaling factor for the original basic impulse response function $CIR_B$, $a_{CFP}$ the scaling factor for the FPP transit correction function $CF_P$, and $a_{CFR}$ the scaling factor for the recirculation correction function $CF_R$.

Figure 8:
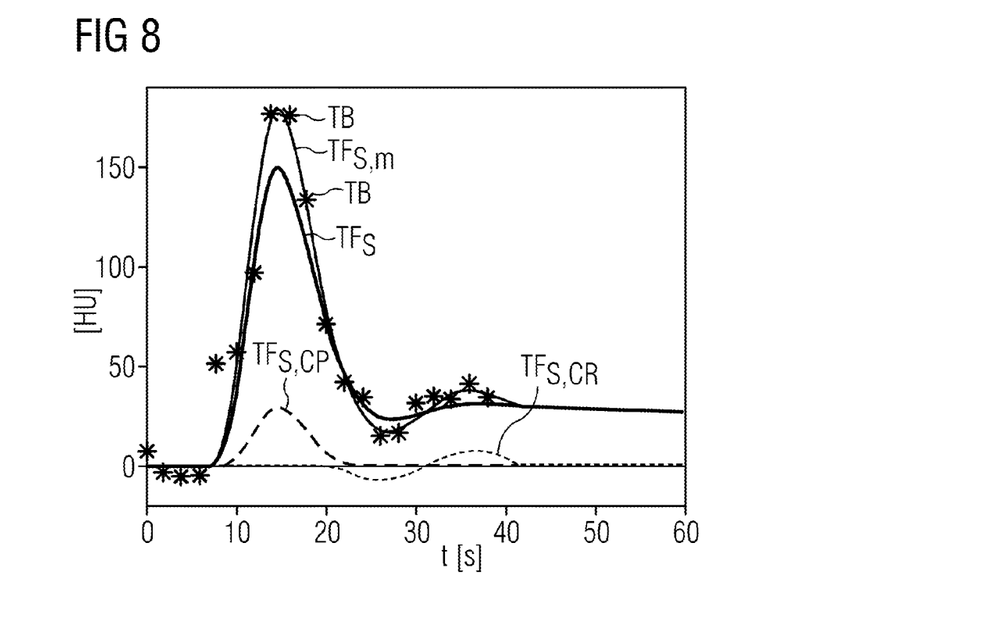
FIG. 8 is a graph showing an example of a basic impulse response function and two function section correction functions. Also shown is test bolus contrast medium behavior data and a simulated test bolus contrast medium behavior function fitted thereto which was formed by superimposing the basic impulse response function and the function section correction functions.

FIG. 8 shows a corresponding fit. Illustrated here is patient-specific test bolus contrast medium behavior data TB to which a test bolus contrast medium behavior function TFS,m is fitted, wherein this simulated test bolus contrast medium behavior function TFS,m is composed of a simulated test bolus behavior function TFS resulting from the convolution of the basic impulse response function CIRB shown in FIG. 7 with the input function, a simulated test bolus FPP behavior function TFS,CP resulting from convolution of the FPP transit correction function CFP shown in FIG. 7 with the input function IF, and a simulated test bolus recirculation behavior function TFS,CR resulting from convolution of the recirculation correction function CFR shown in FIG. 7 with the input function IF. This graph clearly shows how an excellent fit to measured test bolus contrast medium behavior data TB is possible with this method.

Depending on the length of the test bolus, i.e. the period of time over which test bolus contrast medium behavior data TB was acquired, it could also be decided, for example, to omit the recirculation correction function CFR from the calculation. In this case the matrix in equation (6) would only consist of two columns, but the fit routine would remain unchanged.

In conclusion, it is once again pointed out that the method described in detail above and the system architecture are merely example embodiments which can be modified in many different ways by the average person skilled in the art without departing from the scope of the invention in so far as it is defined in the claims. In particular, combinations of the described methods are also possible, i.e. both the selection of a basic impulse response function from a plurality of e.g. patient-type-specific basic impulse response functions and the use of an FPP transit correction function and/or a recirculation correction function or other correction functions, for example. For the sake of completeness, it is also pointed out that the use of the indefinite article "a" or "an" does not rule out that the features in question may also be present on a multiple basis. Likewise, the term "unit" does not exclude the possibility that these consist of a plurality of components that may also be spatially distributed.

What is claimed is:

1. A method for determining a patient-specific contrast medium impulse response function, comprising:
   providing patient-specific test bolus contrast medium behavior data based on a defined test bolus input function;
   providing basic impulse response functions;
   generating simulated test bolus contrast medium behavior functions by combining the basic impulse response functions with the test bolus input function;
   fitting the simulated test bolus contrast medium behavior functions and the patient-specific test bolus contrast medium behavior data to one another by varying fitting parameters to obtain optimum fitting parameter values;
   creating the patient-specific contrast medium impulse response function on the basis of the basic impulse response functions and the optimum fitting parameter values; and
   controlling an imaging scanner based on the patient-specific contrast medium impulse response function.

2. The method of claim 1, wherein at least one of the basic impulse response functions is based on empirical data.

3. The method of claim 2, wherein at least one of the basic impulse response functions is based on a population-averaged contrast medium impulse response function.

4. The method of claim 2, wherein a plurality of the basic impulse response functions are provided.

5. The method of claim 2, wherein the fitting includes using at least one function section correction function.

6. The method of claim 2, wherein the optimum fitting parameter values for the basic impulse response functions are determined using iteration by,
   scaling the basic impulse response functions using a time scaling factor,
   determining a current simulated test bolus contrast medium behavior function for the time-scaled basic impulse response functions,
   fitting the current simulated test bolus contrast medium behavior function and the patient-specific test bolus contrast medium behavior data to one another by varying additional fitting parameters,
   determining a deviation value of the currently fitted simulated test bolus contrast medium behavior function from the patient-specific test bolus contrast medium behavior data, and storing the parameter value combination of the current fitted simulated test bolus contrast medium behavior function if the deviation value is better than a deviation value of a previously stored parameter value combination, wherein the time scaling factor is varied from one iteration to a next iteration and the iteration is continued until a termination criterion is achieved.

7. The method of claim 2, wherein a basic impulse response function is selected using iteration by, selecting a basic impulse response function from the plurality of basic impulse response functions, and determining the optimum fitting parameter values for the selected basic impulse response function, wherein from one iteration to a next iteration, a new basic impulse response function is selected from the plurality of basic impulse response functions and the iteration is continued until a termination criterion is achieved.

8. The method of claim 1, wherein a plurality of the basic impulse response functions are provided.

9. The method of claim 1, wherein the fitting includes using at least one function section correction function.

10. The method of claim 1, wherein at least one of the fitting parameters of at least one of the simulated test bolus contrast medium behavior functions and the test bolus contrast medium behavior data incorporates a time scaling factor.

11. The method of claim 1, wherein at least one of the fitting parameters of at least one of the simulated test bolus contrast medium behavior functions and the test bolus contrast medium behavior data incorporates at least one of an offset time and an amplitude scaling factor.

12. The method of claim 1, wherein the optimum fitting parameter values for the basic impulse response functions are determined using iteration by, scaling the basic impulse response functions using a time scaling factor, determining a current simulated test bolus contrast medium behavior function for the time-scaled basic impulse response functions, fitting the current simulated test bolus contrast medium behavior function and the patient-specific test bolus contrast medium behavior data to one another by varying additional fitting parameters, determining a deviation value of the currently fitted simulated test bolus contrast medium behavior function from the patient-specific test bolus contrast medium behavior data, and storing the parameter value combination of the current fitted simulated test bolus contrast medium behavior function if the deviation value is better than a deviation value of a previously stored parameter value combination, wherein the time scaling factor is varied from one iteration to a next iteration and the iteration is continued until a termination criterion is achieved.

13. The method of claim 12, wherein the current simulated test bolus contrast medium behavior function and the patient-specific test bolus contrast medium behavior data are fitted to one another by varying at least one of an offset time and an amplitude scaling factor.

14. The method of claim 1, wherein a basic impulse response function is selected using iteration by, selecting a basic impulse response function from the plurality of basic impulse response functions, and determining the optimum fitting parameter values for the selected basic impulse response function, wherein from one iteration to a next iteration, a new basic impulse response function is selected from the plurality of basic impulse response functions and the iteration is continued until a termination criterion is achieved.

15. A method for predicting a likely contrast medium behavior by combining the contrast medium impulse response function determined according to claim 1 with an input function.

16. A method for controlling a medical imaging system, the method comprising:

controlling the medical imaging system based on the patient-specific contrast medium impulse response function, wherein a reference time for the imaging system is determined on the basis of a contrast medium injection start time and a contrast medium behavior predicted in accordance with claim 15.

17. A non-transitory computer program product, directly loadable into a memory of a control device of an imaging system, comprising program code segments for carrying out the method of claim 1 when the computer program product is run on the control device.

18. An apparatus to determine a patient-specific contrast medium impulse response function, comprising:

an input interface configured to import data from an imaging scanner or a memory, the data including patient-specific test bolus contrast medium behavior data based on a defined test bolus input function and basic impulse response functions; and a processor configured to, generate simulated test bolus contrast medium behavior functions by combining the basic impulse response functions with the test bolus input function, fit the simulated test bolus contrast medium behavior functions and the patient-specific test bolus contrast medium behavior data to one another by varying fitting parameters to obtain the optimum fitting parameter values, create the patient-specific contrast medium impulse response function on the basis of the basic impulse response functions and the optimum fitting parameter values, and control the imaging scanner based on the patient-specific contrast medium impulse response function.

19. A control device for an imaging system, comprising:

an interface configured to acquire or output a contrast medium injection start time; and the apparatus configured to determine a patient-specific contrast medium impulse response function of claim 18, wherein the processor is configured to determine a reference time for the imaging system based on the contrast medium injection start time and the patient-specific contrast medium impulse response function.

20. An imaging system to produce image data sets of the interior of an examination object, comprising the control device of claim 19.

* * * * *